United States Patent [19]

Beard

[11] Patent Number: 4,640,279

[45] Date of Patent: Feb. 3, 1987

[54] COMBINATION SURGICAL SCALPEL AND ELECTROSURGICAL INSTRUMENT

[75] Inventor: Robert W. Beard, Placerville, Calif.

[73] Assignee: Oximetrix, Inc., Mountain View, Calif.

[21] Appl. No.: 763,549

[22] Filed: Aug. 8, 1985

[51] Int. Cl.⁴ .............................................. A61B 17/36
[52] U.S. Cl. ............................ 128/303.14; 128/303.17
[58] Field of Search ............ 128/303.1, 303.13–303.17

[56] References Cited

U.S. PATENT DOCUMENTS

| | | |
|---|---|---|
| Re. 29,088 | 12/1976 | Shaw . |
| Re. 30,190 | 1/1980 | Shaw . |
| 1,945,327 | 1/1934 | Morse .............................. 128/303.17 |
| 2,447,169 | 8/1948 | De Sousa ........................ 128/303.14 |
| 3,648,001 | 3/1972 | Anderson et al. .............. 128/303.14 |
| 3,911,241 | 10/1975 | Jarrard ............................ 128/303.17 |
| 4,034,761 | 7/1977 | Prater et al. .................... 128/303.17 |
| 4,089,336 | 5/1978 | Cage et al. . |
| 4,091,813 | 5/1978 | Shaw et al. . |
| 4,112,950 | 9/1978 | Pike . |
| 4,185,632 | 1/1980 | Shaw . |
| 4,311,145 | 1/1982 | Esty et al. . |
| 4,375,218 | 3/1983 | DiGeronimo ................... 128/303.17 |
| 4,427,006 | 1/1984 | Nottke . |
| 4,481,057 | 11/1984 | Beard ............................. 128/303.14 |
| 4,562,838 | 1/1986 | Walker ........................... 128/303.17 |

Primary Examiner—Edward M. Coven
Assistant Examiner—Max F. Hindenburg
Attorney, Agent, or Firm—Martin L. Katz; Allan J. Sternstein; Robert W. Stevenson

[57] ABSTRACT

A surgical instrument includes a handle and a disposable assembly which can be readily replaced after each operation or as necessary. The disposable assembly includes both an electrically heated scalpel blade and an electrosurgical active electrode which are mounted in a spaced parallel arrangement so that they can be used alternately by rotating the instrument by 180 degrees. The mounted ends of both the blade and the electrode are adapted to be received by separate terminals in the instrument handle so that the appropriate external power sources can be selectively connected thereto.

12 Claims, 15 Drawing Figures

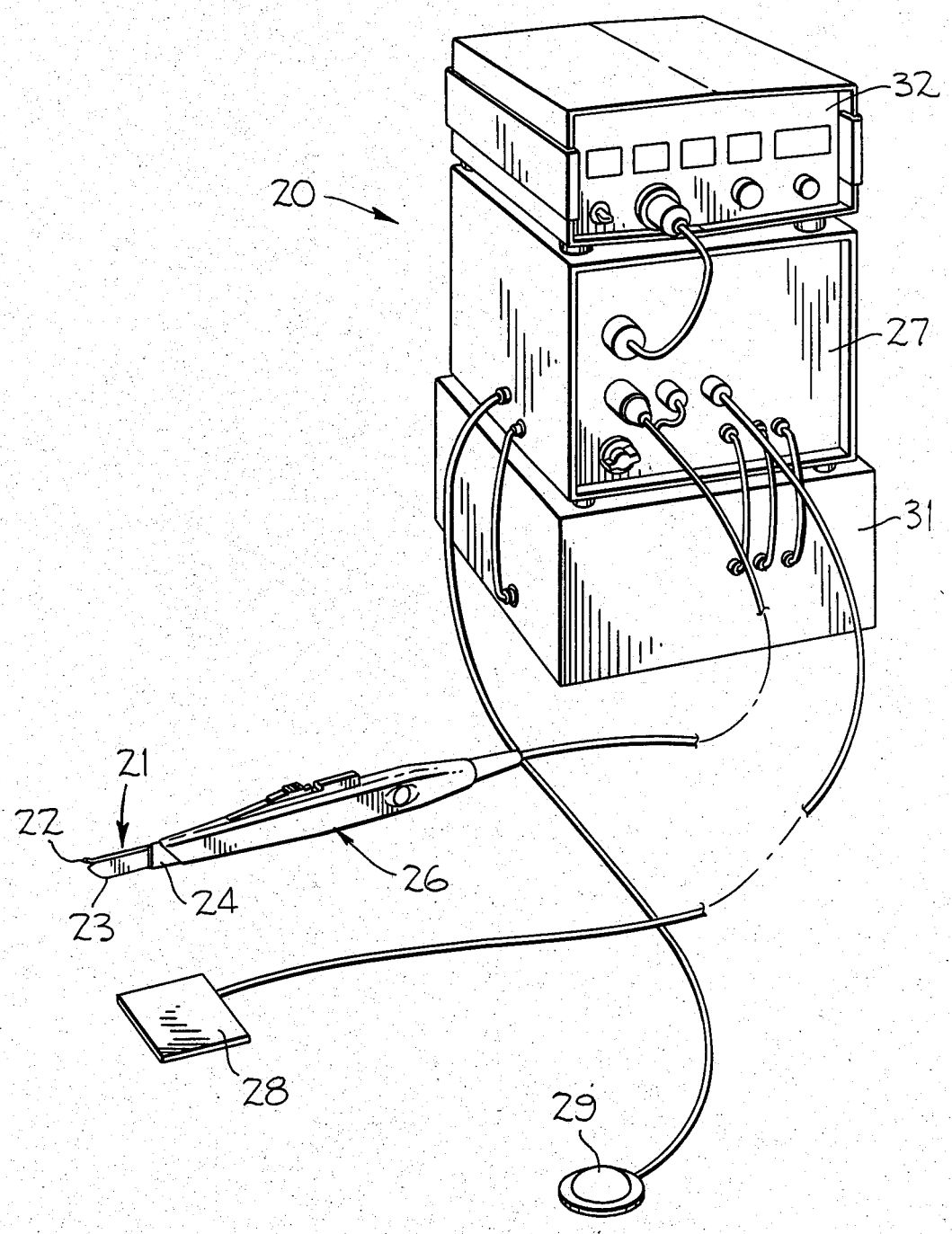
FIG_1

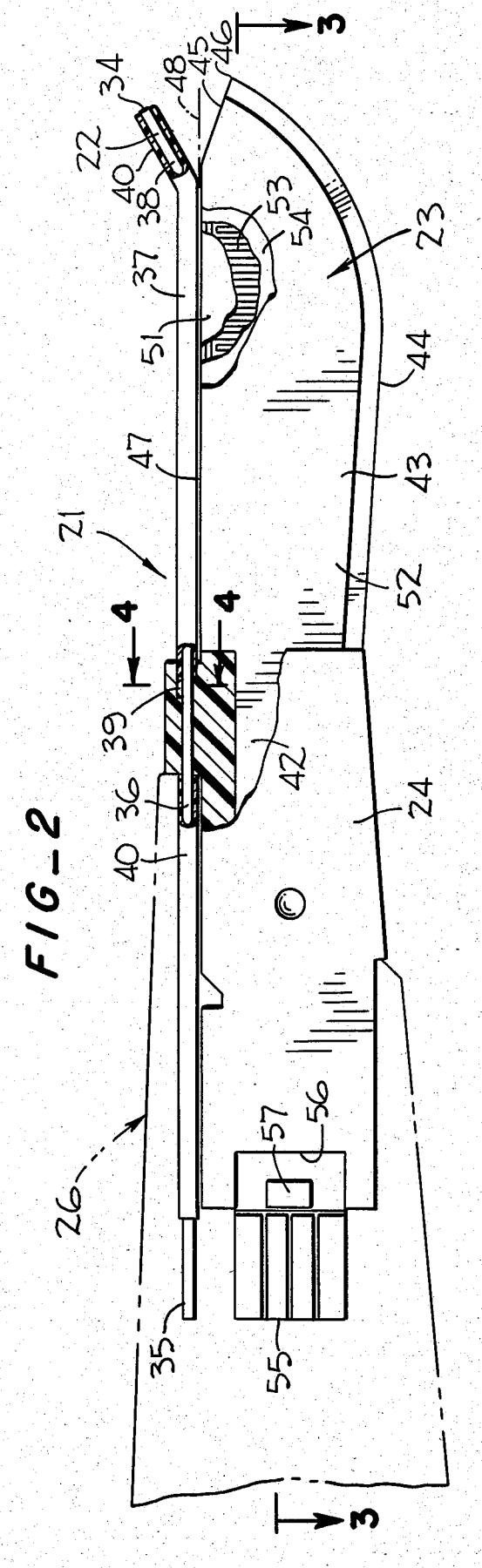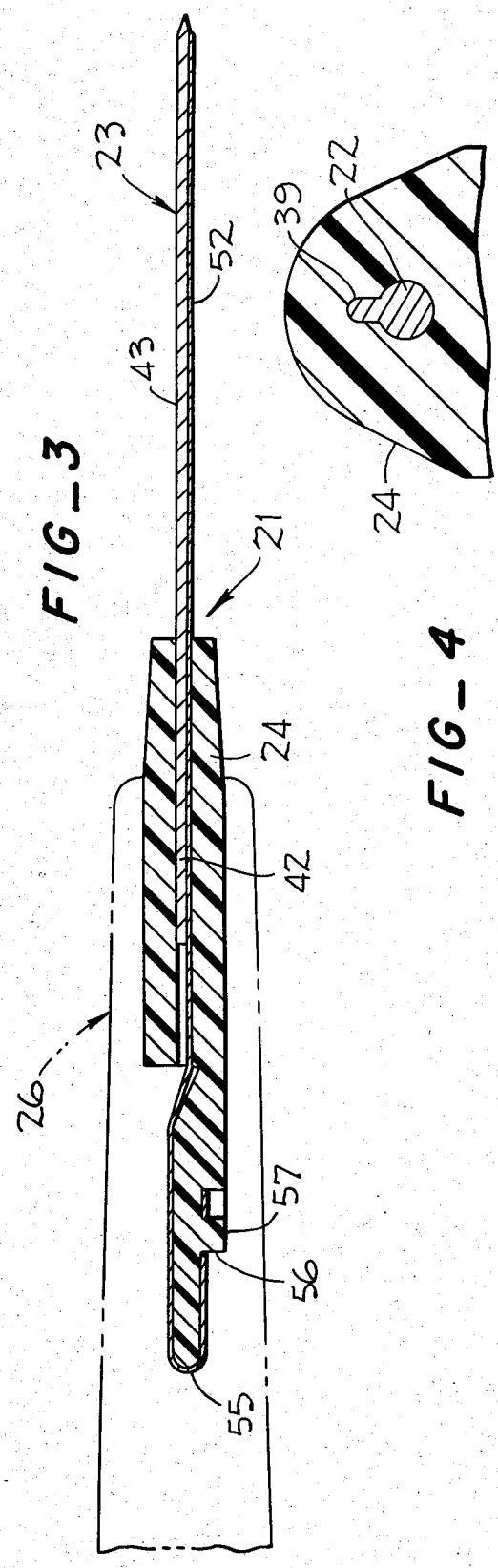

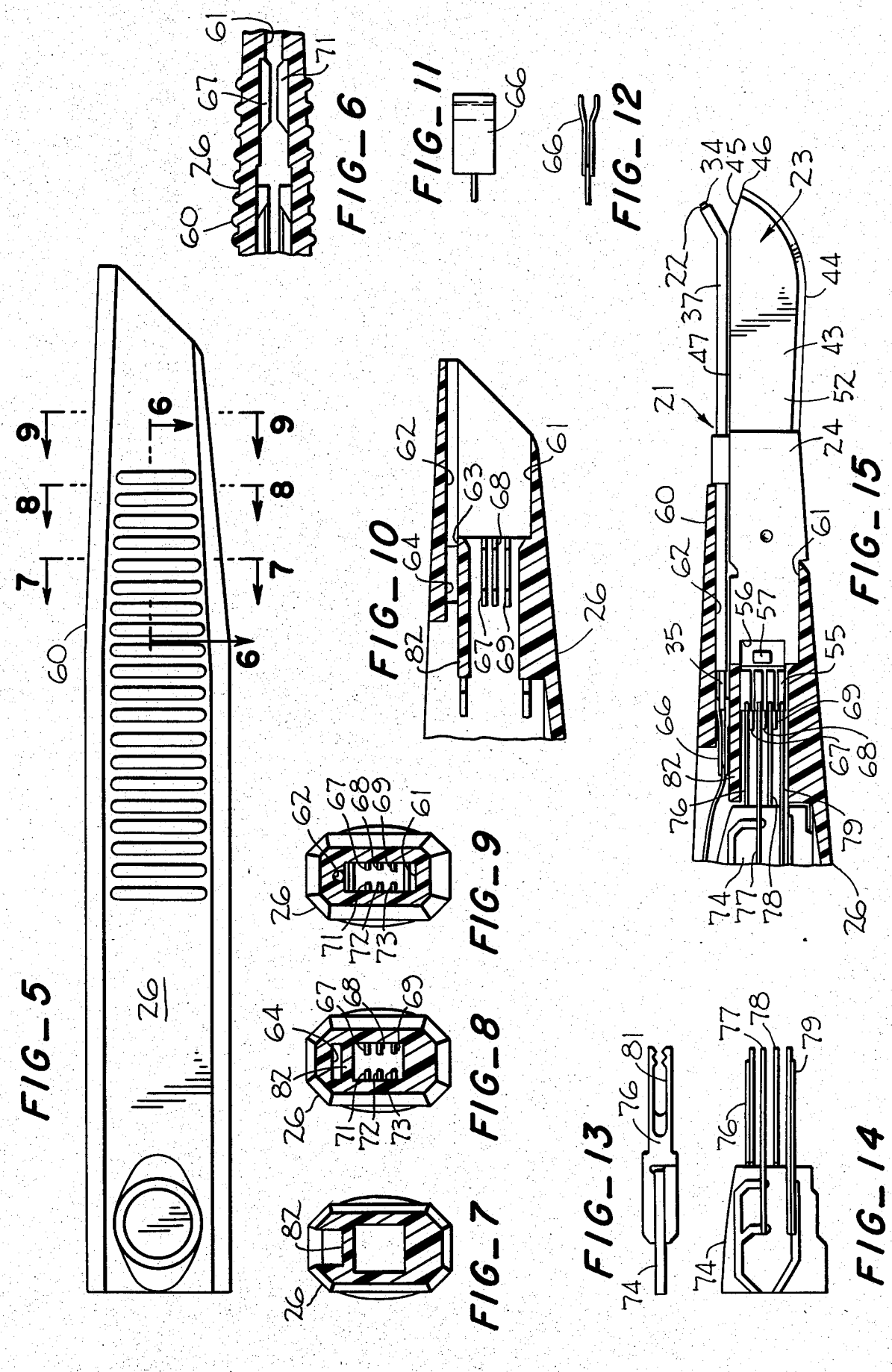

COMBINATION SURGICAL SCALPEL AND ELECTROSURGICAL INSTRUMENT

BACKGROUND OF THE INVENTION

1. Field of the Invention

This invention pertains to surgical instruments, and more particularly it pertains to surgical instruments that apply heat or energy to achieve hemostasis or coagulation for the sealing of blood vessels during the surgical operation.

2. Description of the Prior Art

During a surgical operation, a major portion of the total time required is used for controlling bleeding. Such bleeding obscures the surgeon's vision, reduces his surgical precision and often makes necessary the following of slow and elaborate procedures. Typically, each bleeding vessel must be grasped in a surgical clamp to stop the flow of blood. The tissue and vessel within each clamp is then tied with pieces of fine thread. Such ligated masses of tissue subsequently die and decompose, retarding healing and encouraging infection.

Heating of a cutting instrument to provide simultaneous hemostasis is disclosed in U.S. Pat. No. RE. 29,088 which issued on Jan. 11, 1977, U.S. Pat. No. RE. 30,190 which issued on Jan. 15, 1980, U.S. Pat. No. 4,089,336 which issued on May 16, 1978, U.S. Pat. No. 4,091,813 which issued on May 30, 1978, U.S. Pat. No. 4,185,632 which issued on Jan. 29, 1980, and U.S. Pat. No. 4,481,057 which issued on Nov. 6, 1984. While a heated cutting instrument of the type disclosed in such patents provides satisfactory hemostasis for smaller blood vessels, it does have difficulty sealing larger vessels.

Electrosurgery provides an alternative method of bleeding control, coagulation, or hemostasis, as well as providing a cutting capability. An electrical current flows through a circuit that begins at a high-frequency oscillator within an electrosurgical unit, goes through an active cable and an active electrode to the patient, and then returns from the patient by way of a dispersive electrode and a cable to the electrosurgical unit. The dispersive electrode has a relatively large contact area to prevent burns to the patient's body, while the relatively small contact area between the tissue and the active electrode tip causes a concentration of current (high current density) that heats the tissue at this point. By raising the temperature of the tissue or cells to the point of changing the protein into coagulum, coagulation or hemostasis is accomplished. Electrosurgical instruments that can produce coagulation are disclosed in U.S. Pat. No. 4,112,950 which issued Sept. 12, 1978, to Pike; U.S. Pat. No. 4,311,145 which issued Jan. 19, 1982, to Esty et al.; and U.S. Pat. No. 4,427,006 which issued Jan. 24, 1984, to Nottke.

Surgical and hemostatic scalpels along with electrosurgical units have been available in operating rooms. Hertofore, scalpels and electrosurgical active electrodes have been separate instruments mounted in separate handles. To use a scalpel and an electrosurgical active electrode sequentially during an operation required excessive handling, changing back and forth from one instrument to the other. This is both time consuming and distracting for the surgeon. Furthermore, after an operation the scalpel blade and the electrode are changed individually in their respective handles.

SUMMARY OF THE INVENTION

Advantages of the invention include simplified handling for sequential use of a scalpel that mechanically cuts tissue and an electrosurgical active electrode that controls bleeding by coagulation, simplified handling for changing both a scalpel blade and an electrode simultaneously, minimized interference of the scalpel blade and the electrode with the operation of each other, and prevention of electrical short circuits between the electrode and a scalpel blade.

In accordance with the present invention, there is provided a disposable assembly for a surgical instrument that cuts tissue mechanically and that applies electrical current thereto causing coagulation. The assembly includes an electrosurgical active electrode, a scalpel and a body that joins the scalpel and the electrode for simultaneous movement and simultaneous support. The electrode has a tip at one end, an electrical contact at the opposite end, and an intermediate portion with a straight section. The scalpel has a shank section and a blade section projecting from the shank section. The blade section has a cutting edge and a back edge that come together at a point remote from the shank section. A straight portion of the blade back edge is positioned adjacent the straight section of the electrode with the electrode tip and the blade section point facing in the same direction. The blade section point is spaced sufficiently from the electrode tip to prevent electrical shorting therebetween. The adjacent straight electrode section and back edge portion define therebetween an axis of rotation. The body holds the scalpel and the electrode in opposed operational positions that are used sequentially by rotating the assembly one half revolution about the axis of rotation.

In a preferred embodiment of the invention, a surgical instrument is provided which includes a disposable assembly as described and a handle to support the assembly. The handle has a socket for receiving a portion of the disposable assembly body and a receptacle for receiving the electrical contact of the electrode.

BRIEF DESCRIPTION OF THE DRAWINGS

FIG. 1 is a perspective view of a combination surgical scalpel and electrosurgical instrument system embodying the present invention.

FIG. 2 is a side elevation view of a disposable assembly for the system of FIG. 1 with portions broken away to show underlying structure and with portions of a handle being indicated in phantom line.

FIG. 3 is a section taken on the line 3—3 of FIG. 2.

FIG. 4 is an enlarged section taken on the line 4—4 of FIG. 2.

FIG. 5 is a side elevation view of a handle, forward section.

FIG. 6 is a horizontal section taken on the line 6—6 of FIG. 5.

FIG. 7 is a transverse vertical section taken on the line 7—7 of FIG. 5.

FIG. 8 is a transverse vertical section taken on the line 8—8 of FIG. 5.

FIG. 9 is a transverse vertical section taken on the line 9—9 of FIG. 5.

FIG. 10 is a longitudinal section in elevation at the forward portion of the handle shown in FIG. 5.

FIG. 11 is a plan view of a receptacle for receiving an electrical contact of an electrosurgical active electrode.

FIG. 12 is an elevational view of the receptacle shown in FIG. 11.

FIG. 13 is a plan view of a receptacle for receiving the support and contact portion of a hemostatic scalpel heating assembly.

FIG. 14 is an elevation view of the receptacle shown in FIG. 13.

FIG. 15 is a longitudinal section in elevation at the forward portion of the handle with the disposable assembly in place in the handle.

DESCRIPTION OF THE PREFERRED EMBODIMENT

Looking now at FIG. 1, a combination surgical, hemostatic and electrosurgical instrument system 20 is shown. In this system, a disposable assembly 21 is provided which includes an electrosurgical active electrode 22 and a hemostatic scalpel blade 23 that are joined together by a body 24 of electrically insulative material. A portion of this body fits into a handle 26 that supports the disposable assembly. The handle is electrically connected to an interface unit 27. A dispersive electrode 28, that is arranged to be positioned on the opposite side of a patient's body from the active electrode, and a foot switch 29, that controls the flow of current to the active electrode, are also electrically connected to the interface unit that contains switching and control circuitry. Also electrically connected to the interface unit are an electrosurgical unit 31 that provides the power for performing electrosurgical cauterization or coagulation with the active electrode and a controller 32 that provides power for heating the hemostatic scalpel blade.

With reference to FIG. 2, it will be seen that electrode 22 has a tip 34 at one end, an electrical contact 35 at the opposite end, and an intermediate portion 36 with a straight section 37. A bend section 38 is located between the straight section and the electrode tip. This bent section diverges away from the scalpel blade 23 and the deflection angle between the straight section and the bent section of the electrode is about 30 degrees so that the tip 34 will be well spaced from the blade 23. A radial projection 39, shown in FIGS. 2 and 4, is provided on the electrode for locking the electrode against axial rotation within the body 24, and the electrode is also locked against axial movement within the body by the radial projection. An insulating sleeve 40 is provided about the electrode between the electrical contact 35 and the tip 34 to avoid electrical shorting between the electrode and the scalpel blade.

The hemostatic scalpel blade 23 has a shank section 42 and a blade section 43. The blade section has a cutting edge 44 and a back edge 45 that come together at a point 46 remote from the shank section. The back edge of the blade section has a straight portion 47 that is positioned adjacent the straight section 37 of the electrode 22 with the electrode tip 34 and the blade section point 46 facing in the same direction. The blade section point is spaced sufficiently from the electrode tip to prevent electrical shorting therebetween. The blade section projects beyond the electrode tip and shields the electrode when the scalpel is in use. The adjacent straight electrode section and the back edge straight portion define therebetween an axis of rotation 48 (FIG. 2).

The hemostatic scalpel blade 23 is of the type disclosed in U.S. Pat No. 4,481,057 and includes a metallic laminate core 51, shown in FIG. 2, formed by a steel substrate, not shown, that is sandwiched between two copper composition laminae. A heating assembly 52 (FIG. 3) has a heater portion 53, shown in FIG. 2, that is formed of a narrow strip of copper foil, an adhesive including thermally conductive filler material advixed with resins securing the heater portion to the core 51 in a thermally conductive but electrically insulative relationship, and a polyimide backing material 54 upon which the heater portion is disposed prior to being attached to the metallic laminate core of the scalpel blade section 43 and which insulates the heater portion from external contacts. After assembly of the heating assembly to the core, the outer surfaces of the scalpel blade section are coated with a non-stick material that is preferably a form of polytetrafluoroethylene and chosen from the group consisting of tetrafluoroethane, polyfluorinated alcoxy and fluorinated ethylene polymer.

The heating assembly 52 has a contact portion 55 that is threaded through the hollow body 24 and wrapped around the rearwardly projecting end of the body, as shown in FIG. 3. An aperture 56 that is provided in the contact portion fits about a peg 57 of the body for securing the contact portion to the body. Preferably, the body is made of thermoplastic material such that peg 57 may be heated so as to expand and heat stake the contact portion of the heating assembly to the body. The shank 42 of the scalpel blade is secured within a narrow channel in the body (FIG. 3). Thus, the body joins the scalpel blade and the electrosurgical active electrode 22 for simultaneous movement and support.

The scalpel handle 26 has a forward section 60, shown in FIG. 5, with internal configurations as illustrated in FIGS. 6-10. This forward section of the handle defines a socket 61 (FIG. 6) having a rectangular cross-sectional configuration for receiving the rearwardly projecting portion of the assembly body 24, as shown in FIG. 15, to support the assembly 21. Penetration of the assembly body into the socket and the minimal clearances therebetween provide a tight fit sufficient for resisting rotational forces on the body due to forces applied to the scalpel blade or the electrode during their use. At the upper side of socket 61 is a coextensive groove 62, shown in FIGS. 9 and 10, for enabling passage of the electrode contact 35 when the assembly body 24 is inserted into the socket 61. At the innermost end of the groove 62 is a bore 63 that is followed by a rectangular slot 64, shown in FIGS. 8 and 10. Fitting within the rectangular slot is a clip receptacle 66, shown in FIGS. 11, 12 and 15, for receiving the electrode contact 35 and making good electrical contact therewith. It will be seen that the clip receptacle is attached to an electrical lead which is connected to the appropriate circuitry for providing a sufficient voltage to the electrode 22.

In the handle forward section 60, spaced inwardly from the socket 61, are a plurality of spaced flanges 67, 68 and 69 projecting laterally inwardly from one side wall and a plurality of spaced flanges 71, 72 and 73 projecting laterally inwardly from the opposite side wall, as shown in FIGS. 6 and 8-10, all of such flanges being formed integrally with the remainder of the handle. A printed circuit board 74, shown in FIGS. 13, 14 and 15, is provided at one end thereof with a plurality of spaced metallic contacts 76, 77, 78 and 79 that are arranged to interfit with the plastic flanges of the handle, as shown in FIGS. 15, so that the flanges insulate the contacts from each other. As can be seen from FIGS. 13 and 14, the contacts 76–79 are opposed prongs that are adapted to yield outwardly when they grip the heater assembly 52. The forwardly directed portion of the contacts define a receptacle 81 (FIG. 13) for receiving the contact portion 55 of the heating assembly 52. A partition 82 in the handle body separates and insulates the electrosurgical clip receptacle 66 from the heating assembly contact receptacle 81. The clip receptacle grips the electrode contact 35, and contacts 76, 77, 78 and 79 grip the contact portion of the heating assembly with sufficient friction to overcome the gravitational forces on the disposable assembly 21 when the handle 26 is inverted.

Before a surgical operation, the combination surgical, hemostatic and electrosurgical instrument system 20 is made ready. A new disposable assembly 21 is inserted into the handle 26 until the clip receptacle 66 grips the electrode contact 35 and the electrical contacts 76, 77, 78 and 79 grip the contact portion 55 of the heating assembly 52. After an operation, the disposable assembly is withdrawn by hand applying sufficient force to overcome the frictional grip of the clip receptacle and the printed circuit board contacts. The disposable assembly is changed after each operation or during an operation as required. Since the assembly body 24 joins the scalpel blade 23 and the electrode 22 for simultaneous movement and for simultaneous support, the scalpel blade and the electrode are changed simultaneously, thus simplifiying the required handling.

During a surgical operation, the body 24 holds the hemostatic scalpel blade 23 and the electrosurgical active electrode 22 in opposed operational positions. A surgeon with the surgical instrument in hand can use the scalpel blade and the electrode sequentially without putting down the instrument. By rotating the handle 26, the disposable assembly 21 can be turned one-half revolution about the axis of rotation 48, changing from one operational position to the other. Since the operational positions of the scalpel blade and the electrode are one-half revolution apart, when one is in use, the other is thereabove and out of the way, minimizing the interference of one with the other. The scalpel blade section 43 projects beyond the electrode tip 34 and shields the electrode 22 when the scalpel blade is in use. Electrical short circuits between the electrode and the scalpel blade are prevented by the insulating sleeve 40 on the electrode, the spacing between the electrode tip and the blade section point 46, and the internal handle partition 82 that insulates the electrode clip receptacle 66 from the heater contact receptacle 81.

From the foregoing description, it will be seen that the present design of a combination surgical, hemostatic and electrosurgical instrument system 20 has the advantages of simplified handling for sequential use of a scalpel blade 23 that mechanically cuts tissue and an electrosurgical active electrode 22 that controls bleeding by coagulation, simplified handling provided by changing both the scalpel blade and the electrode simultaneously, minimized interference of the scalpel blade and the electrode with each other, and the prevention of electrical short circuits between the electrode and the scalpel blade.

Although the best mode contemplated for carrying out the present invention has been herein shown and described, it will be apparent that modification and variation may be made without departing from what is regarded to be the subject matter of the invention.

I claim:

1. A disposable assembly for a surgical instrument that cuts tissue mechanically and that applies electrical current to the tissue for causing coagulation, said assembly comprising:
   an electrosurgical active electrode having
      a tip at one end,
      and electrical contact at the opposite end, and
      an intermediate portion with a straight section;
   a scalpel blade having
      a shank section and
      a blade section projecting from the shank section, said blade section having
         a cutting edge and
         a back edge that come together at a point remote from the shank section, the back edge including a straight portion positioned adjacent the straight section of the electrode with the electrode tip and the blade section point facing the same direction, the blade section point being spaced sufficiently from the electrode tip to prevent electrical shorting therebetween, the adjacent straight electrode section and back edge straight portion defining therebetween an axis of rotation; and
   a body of electrically insulative material that joins the scalpel blade and the electrode for simultaneous movement and for simultaneous support, said body holding the scalpel blade and the electrode in spaced and opposed operational positions that are used sequentially by rotating the assembly one-half revolution about the axis of rotation.

2. A surgical instrument for cutting tissue mechanically and for applying electrical current to the tissue for causing coagulation, said instrument comprising:
   a disposable assembly that includes
      an electrosurgical active electrode having
         a tip at one end,
         an electrical contact at the opposite end, and
         an intermediate portion with a straight section;
      a scalpel blade having a shank section, and a blade section projecting from the shank section, said blade section having a cutting edge and a back edge that come together at a point remote from the shank section, the back edge including a straight portion positioned adjacent the straight section of the electrode with the electrode tip and the blade section point facing the same direction, the blade section point being spaced sufficiently from the electrode tip to prevent electrical shorting therebetween, the adjacent straight electrode section and back edge straight portion defining therebetween an axis of rotation; and
      a body of electrically insulative material that joins the scalpel blade and the electrode for simultaneous movement and for simultaneous support, said body holding the scalpel blade and the electrode in spaced and opposed operational positions that are used sequentially by rotating the assembly one-half revolution about the axis of rotation; and
   a handle having
      a socket for receiving a portion of the assembly body to support the assembly, and
      a receptacle for receiving the electrode electrical contact.

3. The surgical instrument of claim 2 wherein said handle has a groove that is located adjacent the socket for enabling passage of the electrode contact to and from the receptacle in the handle.

4. The surgical instrument of claim 2 wherein said scalpel blade is a hemostatic scalpel blade, said blade further including a heating assembly with heater and electrical contact portions integrally fabricated from an electrically conductive strip material, said heater portion being attached to the scalpel blade section, said body having a support projecting in the opposite direction from the scalpel blade section, said contact portion of the heating assembly passing through the body and being wrapped around the body support, and said handle including a receptacle for receiving the support and the contact portion of the heating assembly.

5. The surgical instrument of claim 4 wherein the receptacle for receiving the body support and the contact portion of the heating assembly comprises a plurality of opposed yieldable prongs.

6. The disposable assembly of claim 1 wherein said scalpel blade is a hemostatic scalpel blade, said assembly further including a heating assembly with heater and contact portions integrally fabricated from an electrically conductive strip material, said heater portion being attached to the scalpel blade section, said body having a support projecting in the opposite direction from the scalpel blade section, said contact portion of the heating assembly passing through the body and being wrapped around the body support.

7. The disposable assembly of claim 1 wherein the electrode has an insulating sleeve between the electrical contact and the tip to avoid electrical shorting between the electrode and the scalpel blade.

8. The disposable assembly of claim 1 wherein the electrode intermediate portion has a bent section between the straight section and the electrode tip, said bent section diverging away from the blade section of the scalpel blade.

9. The disposable assembly of claim 8 wherein the deflection angle between the straight section and the bent section is about 30 degrees.

10. The disposable assembly of claim 1 wherein the intermediate portion of the electrode has a radial deformation for locking the electrode against axial rotation within the body.

11. The disposable assembly of claim 1 including means for locking the electrode against axial movement within the body.

12. The disposable assembly of claim 1 wherein the scalpel blade section projects beyond the electrode tip and shields the electrode when the scalpel blade is in use.

* * * * *